(12) United States Patent
Ito

(10) Patent No.: US 12,246,303 B2
(45) Date of Patent: Mar. 11, 2025

(54) WATER-ABSORBING RESIN PARTICLES AND ABSORBENT ARTICLE

(71) Applicant: SUMITOMO SEIKA CHEMICALS CO., LTD., Hyogo (JP)

(72) Inventor: Takashi Ito, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 954 days.

(21) Appl. No.: 17/298,822

(22) PCT Filed: Dec. 12, 2019

(86) PCT No.: PCT/JP2019/048798
§ 371 (c)(1),
(2) Date: Jun. 1, 2021

(87) PCT Pub. No.: WO2020/122203
PCT Pub. Date: Jun. 18, 2020

(65) Prior Publication Data
US 2022/0016597 A1   Jan. 20, 2022

(30) Foreign Application Priority Data

| Dec. 12, 2018 | (JP) | ................................ 2018-232848 |
| Jan. 30, 2019 | (JP) | ................................ 2019-014517 |
| Mar. 22, 2019 | (JP) | ................................ 2019-055262 |
| Mar. 22, 2019 | (JP) | ................................ 2019-055311 |

(51) Int. Cl.
| B01J 20/26 | (2006.01) |
| A61F 13/539 | (2006.01) |
| B01J 20/28 | (2006.01) |
| G01N 21/59 | (2006.01) |
| A61F 13/53 | (2006.01) |
| A61L 15/24 | (2006.01) |

(52) U.S. Cl.
CPC ........... *B01J 20/267* (2013.01); *A61F 13/539* (2013.01); *B01J 20/28004* (2013.01); *B01J 20/28016* (2013.01); *G01N 21/59* (2013.01); *A61F 2013/530569* (2013.01); *A61F 2013/530591* (2013.01); *A61F 2013/530729* (2013.01); *A61F 2013/53908* (2013.01); *A61L 15/24* (2013.01)

(58) Field of Classification Search
CPC .... B01J 20/26; B01J 20/267; B01J 20/28004; B01J 20/28016; A61F 13/539; A61F 2013/530569; A61F 2013/530591; A61F 2013/530729; A61F 2013/53908; G01N 21/59; A61L 15/24
USPC ........................................................ 502/402
See application file for complete search history.

(56) References Cited

U.S. PATENT DOCUMENTS

| 2016/0280825 A1 | 9/2016 | Bauer et al. |
| 2017/0266640 A1 | 9/2017 | Mark et al. |

FOREIGN PATENT DOCUMENTS

| CN | 1916032 | 2/2007 |
| CN | 103703028 | 4/2014 |
| EP | 1029886 | 8/2000 |
| EP | 1097946 | 5/2001 |
| EP | 1433526 | 6/2004 |
| EP | 2893974 | 7/2015 |
| EP | 2993189 | 3/2016 |
| EP | 3015525 | 5/2016 |
| EP | 3895676 | 10/2021 |
| EP | 3896096 | 10/2021 |
| EP | 3896097 | 10/2021 |
| EP | 3896119 | 10/2021 |
| EP | 3936225 | 1/2022 |
| EP | 3936549 | 1/2022 |
| JP | H2-191604 | 7/1990 |
| JP | H2-196802 | 8/1990 |
| JP | H6-345819 | 12/1994 |
| JP | H8-020640 | 1/1996 |
| JP | H9-510889 | 11/1997 |
| JP | H11-071425 | 3/1999 |
| JP | H11-080248 | 3/1999 |
| JP | H11-349687 | 12/1999 |
| JP | 2000-302876 | 10/2000 |
| JP | 2001-098170 | 4/2001 |
| JP | 2001-131210 | 5/2001 |
| JP | 2006-008896 | 1/2006 |
| JP | 2007-077393 | 3/2007 |
| JP | 2007-119721 | 5/2007 |
| JP | 2009-051952 | 3/2009 |
| JP | 2009-203383 | 9/2009 |
| JP | 2013-226278 | 11/2013 |
| JP | 2014-014818 | 1/2014 |
| JP | 2014-039684 | 3/2014 |
| JP | 2016-032588 | 3/2016 |
| JP | 2017-502094 | 1/2017 |
| JP | 2017-538008 | 12/2017 |
| JP | 2018-127508 | 8/2018 |
| JP | 2018-187545 | 11/2018 |
| WO | 95/026209 | 10/1995 |
| WO | 2007/011058 | 1/2007 |

(Continued)

OTHER PUBLICATIONS

International Preliminary Report on Patentability of PCT/JP2019/048798, Jun. 24, 2021, 12 pages.
Fujita, Sayaka, "Development of new superabsorbent polymer indicating biodegradability and its performance evaluation", The 25th (2011) Open up originality, Advanced technology award, Special award-winning paper, 2011, p. 1-10; https://www.fbiaward.jp/sentan/jusyou/2011/4.pdf; Partial translation provided.
International Search Report of PCT/JP2019/048798, Mar. 3, 2020, 2 pages.

(Continued)

*Primary Examiner* — Edward M Johnson
(74) *Attorney, Agent, or Firm* — HSML P.C.

(57) ABSTRACT

Water-absorbing resin particles, in which a light transmittance at a wavelength of 425 nm when the water-absorbing resin particles are swollen 30 times with a physiological saline solution is 20% or more, are disclosed.

10 Claims, 2 Drawing Sheets

(56) References Cited

FOREIGN PATENT DOCUMENTS

| WO | 2008/108277 | 9/2008 |
|---|---|---|
| WO | 2011/040530 | 4/2011 |
| WO | 2011/086843 | 7/2011 |
| WO | 2014/208316 | 12/2014 |
| WO | 2015/062883 | 3/2015 |
| WO | 2015/198929 | 12/2015 |
| WO | 2016/087262 | 6/2016 |
| WO | 2016/104374 | 6/2016 |

OTHER PUBLICATIONS

"List of rotors", Kokusan Co. Ltd., 2015, 3 pages; Partial translation provided.
"Certificate of Experimental Results, Opponent's Exhibit No. 15", submitted for Japanese Patent Application No. 2019-055262, Apr. 28, 2021, 4 pages; English translation provided.
"Certificate of Experimental Results, Opponent's Exhibit No. 16", submitted for Japanese Patent Application No. 2019-055262, Apr. 28, 2021, 4 pages; English translation provided.
"Certificate of Experimental Results, Opponent's Exhibit No. 17", submitted for Japanese Patent Application No. 2019-055262, Apr. 28, 2021, 6 pages; English translation provided.
"Certificate of Experimental Results, Opponent's Exhibit No. 18", submitted for Japanese Patent Application No. 2019-055262, Apr. 28, 2021, 6 pages; English translation provided.
"Certificate of Experimental Results, Opponent's Exhibit No. 19", submitted for Japanese Patent Application No. 2019-055262, Apr. 28, 2021, 4 pages; English translation provided.
Fredric L et al., "Modern Superabsorbent Polymer Technology", 1998, pp. 69-74 and 251-257.
"Certificate of Experimental Results, Opponent's Exhibit No. 17", submitted for Japanese Patent Application No. 2019-055311, Apr. 28, 2021, 6 pages; English translation provided.
"Certificate of Experimental Results, Opponent's Exhibit No. 18", submitted for Japanese Patent Application No. 2019-055311, Apr. 28, 2021, 6 pages; English translation provided.
"Certificate of Experimental Results, Opponent's Exhibit No. 19", submitted for Japanese Patent Application No. 2019-055311, Apr. 28, 2021, 4 pages; English translation provided.
"Certificate of Experimental Results, Opponent's Exhibit No. 20", submitted for Japanese Patent Application No. 2019-055311, Apr. 28, 2021, 4 pages; English translation provided.
"Certificate of Experimental Results, Opponent's Exhibit No. 21", submitted for Japanese Patent Application No. 2019-055311, Apr. 28, 2021, 4 pages; English translation provided.
Notice of reasons for cancellation issued for Japanese Patent Application No. 2019-055311 (Patent No. 6775050), Feb. 1, 2022, 25 pages; English translation provided.
"Certificate of Experimental Results, Reference Document 1", Nov. 16, 2021, 2 pages; English translation provided.
"Certificate of Experimental Results, Reference Document 2", Nov. 16, 2021, 2 pages; English translation provided.
"Certificate of Experimental Results, Reference Document 3", Nov. 16, 2021, 2 pages; English translation provided.
Notice of reasons for cancellation issued for Japanese Patent Application No. 2019-055262 (Patent No. 6775048), Feb. 1, 2022, 25 pages; English translation provided.
Notice of Reasons for Cancellation issued for Japanese Patent Application No. 2019-055262 (Patent No. 6775048), Aug. 12, 2021, 104 pages including English translation.
Notice of Reasons for Cancellation issued for Japanese Patent Application No. 2019-055311 (Patent No. 6775050), Aug. 12, 2021, 122 pages including English translation.
The extended European Search Report issued for European Patent Application No. 19895357.2, Aug. 10, 2022, 20 pages.

WATER-ABSORBING RESIN PARTICLES AND ABSORBENT ARTICLE

TECHNICAL FIELD

The present invention relates to water-absorbing resin particles, a method for evaluating liquid leakage properties of water-absorbing resin particles, and a method for producing water-absorbing resin particles. The present invention further relates to an absorbent article.

BACKGROUND ART

Conventionally, an absorbent containing water-absorbing resin particles has been used in an absorbent article for absorbing a liquid containing water such as urine as a main component. For example, Patent Literature 1 below discloses a method for producing water-absorbing resin particles having a particle size that enables them to be suitably used for an absorbent article such as a diaper, and Patent Literature 2 below discloses a method of using a hydrogel-absorbent polymer having flow inducibility for a specific saline solution, performance under pressure, and the like as an effective absorbent member for accommodating various body fluids such as urine.

CITATION LIST

Patent Literature

[Patent Literature 1] Japanese Unexamined Patent Publication No. H6-345819
[Patent Literature 2] Published Japanese Translation No. H9-510889 of the PCT International Publication

SUMMARY OF INVENTION

Technical Problem

An absorbent article formed from a conventional absorbent has room for improvement in leakage properties in which because an absorption target liquid is not sufficiently absorbed by the absorbent, a phenomenon (liquid running) in which the excess liquid flows on a surface of the absorbent is likely to occur, and as a result, the liquid leaks to the outside of the absorbent article.

An object of one aspect of the present invention is to provide water-absorbing resin particles capable of inhibiting liquid leakage. An object of another aspect of the present invention is to provide an absorbent article in which liquid leakage is inhibited.

Solution to Problem

One aspect of the present invention provides water-absorbing resin particles in which a light transmittance at a wavelength of 425 nm when the water-absorbing resin particles are swollen 30 times with a physiological saline solution is 20% or more.

As a result of diligent studies on reduction of liquid leakage, the inventors of the present invention have found that liquid leakage is effectively inhibited in a case where a light transmittance at a wavelength of 425 nm when the water-absorbing resin particles are swollen 30 times with a physiological saline solution is 20% or more. It is thought that, in a case where the liquid smoothly permeates the water-absorbing resin particles and thereby the entire particles are swollen uniformly, light scattering of a swollen gel is less likely to occur.

In the water-absorbing resin particles, a water retention capacity for a physiological saline solution may be 30 to 55 g/g.

Another aspect of the present invention provides a method for evaluating liquid leakage properties of water-absorbing resin particles. In this method, an effect of inhibiting liquid leakage of the water-absorbing resin particles is evaluated to be high in a case where a light transmittance of the water-absorbing resin particles at a wavelength of 425 nm when these particles are swollen 30 times with a physiological saline solution is 20% or more.

Still another aspect of the present invention provides a method for producing water-absorbing resin particles. This production method includes measuring a light transmittance of the water-absorbing resin particles at a wavelength of 425 nm when these particles are swollen 30 times with a physiological saline solution.

Still another aspect of the present invention provides an absorbent article including a liquid-impermeable sheet, an absorbent, and a liquid-permeable sheet. In the absorbent article, the liquid-impermeable sheet, the absorbent, and the liquid-permeable sheet are disposed in this order. The absorbent contains water-absorbing resin particles, and a light transmittance of the water-absorbing resin particles at a wavelength of 425 nm when these particles are swollen 30 times with a physiological saline solution is 20% or more.

In the above absorbent article, the liquid-permeable sheet may include thermal bonded non-woven fabrics, air through non-woven fabrics, resin bonded non-woven fabrics, spun-bond non-woven fabrics, melt-blown non-woven fabrics, airlaid non-woven fabrics, spunlace non-woven fabrics, point-bonded non-woven fabrics, or a laminate of two or more of non-woven fabrics selected from these non-woven fabrics.

In the above absorbent article, the absorbent may further contain a fibrous material. The absorbent article may further include a core wrap that covers at least a surface side of the absorbent in contact with the liquid-permeable sheet. In the above absorbent article, the absorbent may be adhered to the liquid-permeable sheet.

In the above absorbent article, a water retention capacity of the water-absorbing resin particles for a physiological saline solution may be 30 to 55 g/g. In the above absorbent article, a water absorption speed of the water-absorbing resin particles for a physiological saline solution may be 30 to 80 seconds.

Advantageous Effects of Invention

According to the one aspect of the present invention, it is possible to provide water-absorbing resin particles capable of inhibiting liquid leakage. According to the other aspect of the present invention, it is possible to provide an absorbent article in which liquid leakage is inhibited.

DESCRIPTION OF EMBODIMENTS

Figure 1:
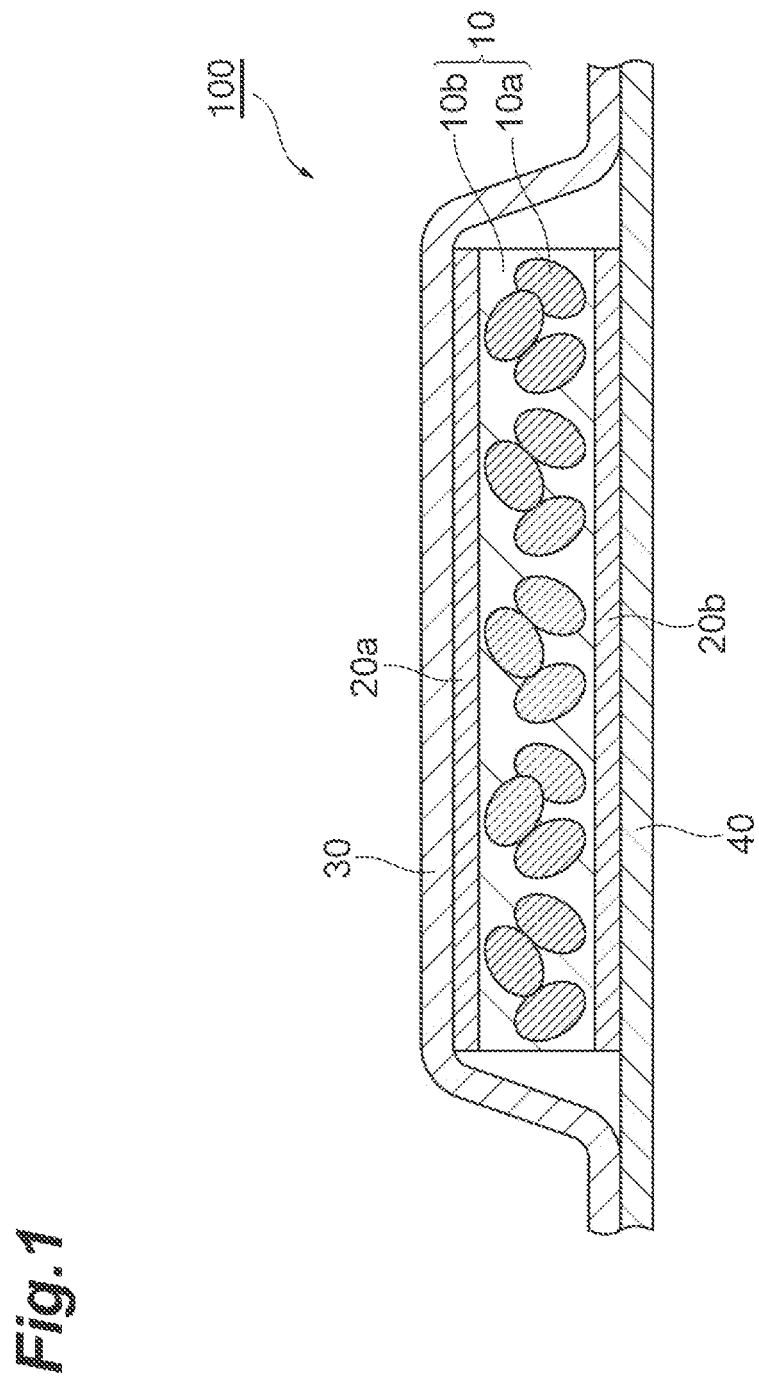
FIG. 1 is a cross-sectional view showing an example of an absorbent article.

Hereinafter, embodiments of the present invention will be described in detail with reference to the drawings as appropriate. However, the present invention is not limited to the following embodiments, and can be variously modified and implemented within the scope of the gist thereof. In the following description, a positional relationship such as low, left, and right is based on a positional relationship shown in the drawings unless otherwise specified. Furthermore, dimensional ratios in the drawings are not limited to the shown ratios.

In the present specification, "acrylic" and "methacrylic" are collectively referred to as "(meth)acrylic." "Acrylate" and "methacrylate" are also referred to as "(meth)acrylate." Regarding numerical value ranges described in a stepwise manner in the present specification, an upper limit value or a lower limit value of a numerical value range in a certain step can be arbitrarily combined with an upper limit value or a lower limit value of a numerical value range in another step. In a numerical value range described in the present specification, an upper limit value or a lower limit value of the numerical value range may be replaced with a value shown in examples. It is sufficient for the expression "A or B" to include any one of A and B, and it may include both of them. The term "water-soluble" means that a solubility of 5% by mass or more is exhibited in water at 25° C. For materials exemplified in the present specification, one kind may be used alone, or two or more kinds may be used in combination. In a case where there are a plurality of substances corresponding to each of components in a composition, a content of each of the components in the composition means a total amount of the plurality of substances present in the composition unless otherwise specified.

A light transmittance of water-absorbing resin particles according to the present embodiment at a wavelength of 425 nm when these particles are swollen 30 times with a physiological saline solution is 20% or more.

The light transmittance at a wavelength of 425 nm when the water-absorbing resin particles are swollen 30 times with a physiological saline solution is measured by the following procedure. First, 0.1 g of the water-absorbing resin particles is put into a quartz cell (for example, a quartz cell manufactured by Tosoh Quartz Corporation: 10 [mm]×10 [mm]× 45 [mm]). 3 g of an aqueous solution of 0.9% by mass sodium chloride (physiological saline solution) which has been adjusted to 25° C. is injected thereinto using a macropipette, and the mixture is left to stand for 30 minutes so that the water-absorbing resin particles absorb the solution. Thereby, a swollen gel layer is produced. Thereafter, defoaming is performed for 10 minutes at a rotational speed of 200 rpm using a centrifuge (for example, product number H-36 manufactured by KOKUSAN Co., Ltd.). After the defoaming, a light transmittance [%] of the swollen gel layer in the quartz cell at 425 nm is measured using a UV measuring device (for example, UV-1850 manufactured by Shimadzu Corporation).

A light transmittance at a wavelength of 425 nm when the water-absorbing resin particles are swollen 30 times with a physiological saline solution is 20% or more. It may be 25% or more, 30% or more, 40% or more, 50% or more, 55% or more, 60% or more, 65% or more, or 70% or more; and it may be 95% or less, 90% or less, 80% or less, 75% or less, 70% or less, or 60% or less. A light transmittance at a wavelength of 425 nm when the water-absorbing resin particles are swollen 30 times with a physiological saline solution may be 20% or more and 95% or less, 25% or more and 90% or less, 30% or more and 80% or less, 40% or more and 80% or less, 50% or more and 80% or less, or 55% or more and 75% or less, from the viewpoint of exhibiting a further better effect of inhibiting liquid leakage.

The water-absorbing resin particles according to the present embodiment can have a high water absorption capacity with respect to a physiological saline solution. A water retention capacity of the water-absorbing resin particles according to the present embodiment for a physiological saline solution may be, for example, 20 g/g or more, 25 g/g or more, 27 g/g or more, 30 g/g or more, 32 g/g or more, 35 g/g or more, 37 g/g or more, 39 g/g or more, or 40 g/g or more, from the viewpoint of appropriately increasing an absorption capacity of an absorbent. A water retention capacity of the water-absorbing resin particles for a physiological saline solution may be 60 g/g or less, 57 g/g or less, 55 g/g or less, 52 g/g or less, 50 g/g or less, 47 g/g or less, 45 g/g or less, or 43 g/g or less. A water retention capacity for a physiological saline solution may be 20 to 60 g/g, 25 to 55 g/g, 30 to 55 g/g, 30 to 50 g/g, or 32 to 42 g/g. Furthermore, a water retention capacity for a physiological saline solution may be 30 to 60 g/g, 32 to 60 g/g, 35 to 55 g/g, 37 to 55 g/g, 39 to 55 g/g, 39 to 52 g/g, 40 to 52 g/g, or 40 to 50 g/g. The water retention capacity for a physiological saline solution is measured by a method described in Examples to be described later.

A water absorption speed of the water-absorbing resin particles according to the present embodiment for a physiological saline solution may be 30 to 80 seconds, 30 to 70 seconds, 30 to 60 seconds, 30 to 50 seconds, 30 to 45 seconds, 35 to 45 seconds, or 35 to 40 seconds. The water absorption speed of the water-absorbing resin particles according to the present embodiment for a physiological saline solution is measured by a method described in Examples to be described later.

Examples of shapes of the water-absorbing resin particles according to the present embodiment include a substantially spherical shape, a crushed shape, and a granular shape. A median particle size of the water-absorbing resin particles according to the present embodiment may be 250 to 850 μm, 300 to 700 μm, or 300 to 600 μm. The water-absorbing resin particles according to the present embodiment may have a desired particle size distribution at a timing obtained in a production method to be described later, but their particle size distribution may be adjusted by performing operations such as adjustment of a particle size through classification with a sieve.

A method for producing the water-absorbing resin particles according to the present embodiment may include a step of measuring a light transmittance of the water-absorbing resin particles at a wavelength of 425 nm when these particles are swollen 30 times with a physiological saline solution. A method for measuring the light transmittance, and the like are as described above.

The water-absorbing resin particles according to the present embodiment can contain, for example, a crosslinked polymer formed by polymerization of monomers including ethylenically unsaturated monomers. The crosslinked polymer has a monomer unit derived from an ethylenically unsaturated monomer. Examples of crosslinked polymers include a hydrolysate of a starch-acrylonitrile graft copolymer, a neutralized product of a starch-acrylic acid graft polymer, a saponified product of a vinyl acetate-acrylic acid ester copolymer, and a partially neutralized polyacrylic acid. Among these crosslinked polymers, the crosslinked polymer may be a partially neutralized polyacrylic acid from the viewpoint of a production amount, manufacturing cost, a water absorption performance, and the like.

The water-absorbing resin particles can be produced by a method including a step of polymerizing monomers including ethylenically unsaturated monomers. Examples of methods of polymerization include a reverse-phase suspension polymerization method, an aqueous solution polymerization method, a bulk polymerization method, and a precipitation polymerization method. Among them, the polymerization method may be the reverse-phase suspension polymerization method or the aqueous solution polymerization method from the viewpoints of facilitating securement of favorable water absorption characteristics of the obtained water-absorbing resin particles and control of a polymerization reaction. Hereinbelow, a method for polymerizing ethylenically unsaturated monomers will be described with the reverse-phase suspension polymerization method as an example.

An ethylenically unsaturated monomer may be water-soluble. Examples thereof include (meth)acrylic acid and a salt thereof, 2-(meth)acrylamide-2-methylpropanesulfonic acid and a salt thereof, (meth)acrylamide, N,N-dimethyl (meth)acrylamide, 2-hydroxyethyl (meth)acrylate, N-methylol (meth)acrylamide, polyethylene glycol mono(meth) acrylate, N,N-diethylaminoethyl (meth)acrylate, N,N-diethylaminopropyl (meth)acrylate, and diethylaminopropyl (meth)acrylamide. In a case where an ethylenically unsaturated monomer has an amino group, the amino group may be quaternarized. The ethylenically unsaturated monomer may be used alone or in a combination of two or more kinds thereof. A functional group, such as a carboxyl group and an amino group, of the monomer, may function as a crosslinkable functional group in a surface crosslinking process to be described later.

Among them, from the viewpoint of high industrial availability, the ethylenically unsaturated monomer may include at least one compound selected from the group consisting of (meth)acrylic acid and a salt thereof, acrylamide, methacrylamide, and N,N-dimethyl acrylamide, or may include at least one compound selected from the group consisting of (meth)acrylic acid and a salt thereof and acrylamide. The ethylenically unsaturated monomer may include at least one compound selected from the group consisting of (meth) acrylic acid and a salt thereof from the viewpoint of further enhancing water absorption characteristics.

For the monomer for obtaining the water-absorbing resin particles, a monomer other than the above-described ethylenically unsaturated monomers may be used. Such a monomer can be used by, for example, being mixed with an aqueous solution containing the above-described ethylenically unsaturated monomers. A usage amount of the ethylenically unsaturated monomers may be 70 to 100 mol %, may be 80 to 100 mol %, may be 90 to 100 mol %, may be 95 to 100 mol %, or may be 100 mol %, with respect to a total amount of monomers. Among them, a proportion of (meth)acrylic acid and a salt thereof may be 70 to 100 mol %, may be 80 to 100 mol %, may be 90 to 100 mol %, may be 95 to 100 mol %, or may be 100 mol %, with respect to a total amount of monomers.

The ethylenically unsaturated monomer may be used in a form of an aqueous solution. A concentration of the ethylenically unsaturated monomers in an aqueous solution containing the ethylenically unsaturated monomers (hereinafter, simply referred to as an "aqueous solution of monomers") may be 20% by mass or more and a saturated concentration or less, may be 25% to 70% by mass, or may be 30% to 55% by mass. Examples of water to be used an aqueous solution include tap water, distilled water, and ion exchange water.

In a case where ethylenically unsaturated monomers have an acidic group, an aqueous solution of monomers may be used after neutralizing this acidic group with an alkaline neutralizing agent. From the viewpoint of increasing an osmotic pressure of the obtained water-absorbing resin particles and thereby further enhancing water absorption characteristics (such as a water retention capacity), a degree of neutralization in the ethylenically unsaturated monomers by the alkaline neutralizing agent may be 10 to 100 mol %, may be 50 to 90 mol %, may be 60 to 80 mol %, or may be 70 to 90 mol % of the acidic group in the ethylenically unsaturated monomers. Examples of alkaline neutralizing agents include alkali metal salts such as sodium hydroxide, sodium carbonate, sodium hydrogen carbonate, potassium hydroxide, and potassium carbonate; and ammonia. The alkaline neutralizing agent may be used alone or in combination of two or more kinds thereof. The alkaline neutralizing agent may be used in a form of an aqueous solution to simplify a neutralizing operation. Neutralization of the acidic groups in the ethylenically unsaturated monomers can be performed by, for example, adding an aqueous solution of sodium hydroxide, potassium hydroxide, or the like dropwise to the above-described aqueous solution of monomers and mixing them.

In the reverse-phase suspension polymerization method, an aqueous solution of monomers can be dispersed in a hydrocarbon dispersion medium in the presence of a surfactant, and polymerization of ethylenically unsaturated monomers can be performed using a radical polymerization initiator or the like. As the radical polymerization initiator, it is possible to use a water-soluble radical polymerization initiator.

Examples of surfactants include nonionic surfactants and anionic surfactants. Examples of nonionic surfactants include sorbitan fatty acid esters, (poly)glycerin fatty acid esters (where "(poly)" means both of a case with the prefix "poly" and a case without the prefix "poly," and the same applies hereinbelow), sucrose fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkylphenyl ethers, polyoxyethylene castor oil, polyoxyethylene hydrogenated castor oil, alkylallyl formaldehyde condensed polyoxyethylene ethers, polyoxyethylene polyoxypropylene block copolymers, polyoxyethylene polyoxypropyl alkyl ethers, and polyethylene glycol fatty acid esters. Examples of anionic surfactants include fatty acid salts, alkylbenzene sulfonate, alkylmethyl taurate, polyoxyethylene alkylphenyl ether sulfuric acid ester salts, polyoxyethylene alkyl ether sulfonic acid salts, phosphoric acid esters of polyoxyethylene alkyl ethers, and phosphoric acid esters of polyoxyethylene alkyl allyl ethers. The surfactant may be used alone or in combination of two or more kinds thereof.

The surfactant may include at least one compound selected from the group consisting of sorbitan fatty acid esters, polyglycerin fatty acid esters, and sucrose fatty acid esters, from the viewpoints that then, a state of a W/O type reverse-phase suspension becomes favorable, water-absorbing resin particles having a suitable particle size are easily obtained, and industrial availability becomes high. The surfactant may include sucrose fatty acid esters or may include sucrose stearic acid esters from the viewpoint that water absorption characteristics of the obtained water-absorbing resin particles are then easily improved.

A usage amount of the surfactant may be 0.05 to 10 parts by mass, may be 0.08 to 5 parts by mass, or may be 0.1 to 3 parts by mass, with respect to 100 parts by mass of the aqueous solution of monomers, from the viewpoint that a sufficient effect is obtained within these usage amounts, and these amounts are economic.

In the reverse-phase suspension polymerization, a polymeric dispersant may be used in combination with the above-mentioned surfactant. Examples of polymeric dispersants include maleic anhydride-modified polyethylene, maleic anhydride-modified polypropylene, a maleic anhydride-modified ethylene-propylene copolymer, a maleic anhydride-modified EPDM (ethylene propylene diene terpolymer), maleic anhydride-modified polybutadiene, a maleic anhydride-ethylene copolymer, a maleic anhydride-propylene copolymer, a maleic anhydride-ethylene-propylene copolymer, a maleic anhydride-butadiene copolymer, polyethylene, polypropylene, an ethylene-propylene copolymer, oxidized polyethylene, oxidized polypropylene, an oxidized ethylene-propylene copolymer, an ethylene-acrylic acid copolymer, ethyl cellulose, ethyl hydroxyethyl cellulose, and the like. The polymeric dispersant may be used alone or in combination of two or more kinds thereof. From the viewpoint of better dispersion stability of monomers, the polymeric dispersant may be at least one selected from the group consisting of maleic anhydride-modified polyethylene, maleic anhydride-modified polypropylene, a maleic anhydride-modified ethylene-propylene copolymer, a maleic anhydride-ethylene copolymer, a maleic anhydride-propylene copolymer, a maleic anhydride-ethylene-propylene copolymer, polyethylene, polypropylene, an ethylene-propylene copolymer, oxidized polyethylene, oxidized polypropylene, and an oxidized ethylene-propylene copolymer.

A usage amount of the polymeric dispersant may be 0.05 to 10 parts by mass, may be 0.08 to 5 parts by mass, or may be 0.1 to 3 parts by mass, with respect to 100 parts by mass of the aqueous solution of monomers, from the viewpoint that a sufficient effect is obtained within these usage amounts, and these amounts are economic.

The hydrocarbon dispersion medium may include at least one compound selected from the group consisting of a chained aliphatic hydrocarbon having 6 to 8 carbon atoms and an alicyclic hydrocarbon having 6 to 8 carbon atoms. Examples of hydrocarbon dispersion media include chained aliphatic hydrocarbons such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, and xylene. The hydrocarbon dispersion medium may be used alone or in combination of two or more kinds thereof.

For the hydrocarbon dispersion medium, at least one selected from the group consisting of n-heptane and cyclohexane may be contained from the viewpoints of high industrial availability and stable qualities. Furthermore, from the same viewpoints, as a mixture of the hydrocarbon dispersion media, for example, a commercially available Exxsol Heptane (manufactured by ExxonMobil Chemical: containing n-heptane and 75% to 85% of hydrocarbons of isomers thereof) may be used.

A usage amount of the hydrocarbon dispersion medium may be 30 to 1,000 parts by mass, may be 40 to 500 parts by mass, or may be 50 to 300 parts by mass, with respect to 100 parts by mass of the aqueous solution of monomers, from the viewpoint that polymerization heat is then appropriately removed, and thereby a polymerization temperature is easily controlled. In a case where a usage amount of the hydrocarbon dispersion medium is 30 parts by mass or more, there is a tendency that it becomes easy to control a polymerization temperature. In a case where a usage amount of the hydrocarbon dispersion medium is 1,000 parts by mass or less, there is a tendency that productivity of polymerization is improved, which is economic.

A radical polymerization initiator may be water-soluble. Examples thereof include persulfates such as potassium persulfate, ammonium persulfate, and sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxyisobutyrate, t-butyl peroxypivalate, and hydrogen peroxide; and azo compounds such as 2,2'-azobis(2-amidinopropane) dihydrochloride, 2,2'-azobis[2-(N-phenylamidino)propane] dihydrochloride, 2,2'-azobis[2-(N-allylamidino)propane] dihydrochloride, 2,2'-azobis[2-(2-imidazolin-2-yl)propane] dihydrochloride, 2,2'-azobis{2-[1-(2-hydroxyethyl)-2-imidazolin-2-yl]propane} dihydrochloride, 2,2'-azobis{2-methyl-N-[1,1-bis(hydroxymethyl)-2-hydroxyethyl]propionamide}, 2,2'-azobis[2-methyl-N-(2-hydroxyethyl)-propionamide], and 4,4'-azobis(4-cyanovaleric acid). The radical polymerization initiator may be used alone or in combination of two or more kinds thereof. The radical polymerization initiator may be at least one selected from the group consisting of potassium persulfate, ammonium persulfate, sodium persulfate, 2,2'-azobis(2-amidinopropane) dihydrochloride, 2,2'-azobis[2-(2-imidazolin-2-yl) propane] dihydrochloride, and 2,2'-azobis{2-[1-(2-hydroxyethyl)-2-imidazolin-2-yl]propane} dihydrochloride.

A usage amount of the radical polymerization initiator may be 0.00005 to 0.01 moles with respect to 1 mole of the ethylenically unsaturated monomers. A case in which a usage amount of the radical polymerization initiator is 0.00005 moles or more is efficient, because then a polymerization reaction is not required to be performed for a long period of time. In a case where a usage amount of the radical polymerization initiator is 0.01 moles or less, it is easy to inhibit occurrence of a rapid polymerization reaction.

The radical polymerization initiator can also be used as a redox polymerization initiator when it is used in combination with a reducing agent such as sodium sulfite, sodium hydrogen sulfite, ferrous sulfate, and L-ascorbic acid.

In a polymerization reaction, an aqueous solution of monomers used for the polymerization may contain a chain transfer agent. Examples of chain transfer agents include hypophosphites, thiols, thiolic acids, secondary alcohols, and amines.

The aqueous solution of monomers used for the polymerization may contain a thickener to control a particle size of the water-absorbing resin particles. Examples of thickeners include hydroxyethyl cellulose, hydroxypropyl cellulose, methyl cellulose, carboxymethyl cellulose, polyethylene glycol, polyacrylamide, polyethyleneimine, dextrin, sodium alginate, polyvinyl alcohol, polyvinylpyrrolidone, polyethylene oxide, and the like. In a case where stirring speeds in the polymerization are the same, a median particle size of particles to be obtained is likely to become large as a viscosity of the aqueous solution of monomers becomes high.

Crosslinking may occur by self-crosslinking upon the polymerization, but crosslinking may be carried out by further using an internal crosslinking agent. By using the internal crosslinking agent, it is easy to control water absorption characteristics of the water-absorbing resin particles. The internal crosslinking agent is generally added to a reaction solution in the polymerization reaction. Examples of internal crosslinking agents include di- or tri(meth)acrylic acid esters of polyols such as ethylene glycol, propylene glycol, trimethylolpropane, glycerin, polyoxyethylene glycol, polyoxypropylene glycol, and polyglycerin; unsaturated polyesters obtained by reacting the polyols with unsaturated acids (such as maleic acid and fumaric acid); bis(meth) acrylamides such as N,N'-methylenebis(meth)acrylamide; di- or tri(meth)acrylic acid esters obtained by reacting a polyepoxide with (meth)acrylic acid; carbamyl di(meth) acrylate esters obtained by reacting a polyisocyanate (such as tolylene diisocyanate and hexamethylene diisocyanate) with hydroxyethyl (meth)acrylate; compounds having two or more polymerizable unsaturated groups, such as allylated starch, allylated cellulose, diallyl phthalate, N,N',N''-triallylisocyanate, and divinylbenzene; polyglycidyl compounds such as (poly)ethylene glycol diglycidyl ether, (poly)propylene glycol diglycidyl ether, (poly)glycerin diglycidyl ether, (poly)glycerin triglycidyl ether, (poly)propylene glycol polyglycidyl ether, and polyglycerol polyglycidyl ether; haloepoxy compounds such as epichlorohydrin, epibromohydrin, and α-methyl epichlorohydrin; compounds having two or more reactive functional groups, such as isocyanate compounds (such as 2,4-tolylene diisocyanate and hexamethylene diisocyanate); and the like. The internal crosslinking agent may be used alone or in combination of two or more kinds thereof. The internal crosslinking agent may be a polyglycidyl compound, may be a diglycidyl ether compound, or may be at least one selected from the group consisting of (poly)ethylene glycol diglycidyl ether, (poly) propylene glycol diglycidyl ether, and (poly)glycerin diglycidyl ether.

A usage amount of the internal crosslinking agent may be 0 mmol or more, 0.02 mmol or more, 0.03 mmol or more, 0.04 mmol or more, or 0.05 mmol or more, and may be 0.1 moles or less, per 1 mole of the ethylenically unsaturated monomer, from the viewpoints of inhibiting water-soluble properties by appropriately crosslinking the obtained polymer, and easily obtaining a sufficient water absorption capacity. In particular, in first-stage polymerization in multistage reverse phase suspension polymerization, when an amount of the internal crosslinking agent is 0.03 mmol or more per 1 mole of the ethylenically unsaturated monomer, it is easy to increase a light transmittance of the swollen water-absorbing resin particles.

An aqueous phase containing an ethylenically unsaturated monomer, a radical polymerization initiator, and if necessary, an internal crosslinking agent, and the like; and an oil phase containing a hydrocarbon dispersant, and if necessary, a surfactant and a polymeric dispersant, and the like can be heated under stirring in a state where they are mixed to carry out reverse-phase suspension polymerization in a water-in-oil system.

When performing the reverse-phase suspension polymerization, an aqueous solution of monomers which contains ethylenically unsaturated monomers is dispersed in a hydrocarbon dispersion medium in the presence of a surfactant (and if necessary, a polymeric dispersant). In this case, a timing of adding the surfactant, the polymeric dispersant, or the like before the start of the polymerization reaction may be either before or after the addition of the aqueous solution of monomers.

Among them, the polymerization may be carried out after dispersing the aqueous solution of monomers in the hydrocarbon dispersion medium in which the polymeric dispersant has been dispersed, and then further dispersing the surfactant in the hydrocarbon dispersion medium, from the viewpoint that an amount of the hydrocarbon dispersion medium remaining in the obtained water-absorbing resin particles can then be easily reduced.

The reverse-phase suspension polymerization can be carried out in one stage or in multiple stages of two or more stages. The reverse-phase suspension polymerization may be carried out in two or three stages from the viewpoint of increasing productivity.

In a case where reverse-phase suspension polymerization is carried out in multiple stages of two or more stages, it is sufficient for stages after a second stage of reverse-phase suspension polymerization to be carried out in the same manner as in a first stage of reverse-phase suspension polymerization by adding ethylenically unsaturated monomers to a reaction mixture obtained in the first stage of polymerization reaction and mixing them, after performing the first stage of reverse-phase suspension polymerization. In reverse-phase suspension polymerization in each stage after the second stage, reverse-phase suspension polymerization may be carried out by adding, in addition to ethylenically unsaturated monomers, the above-mentioned radical polymerization initiator and/or internal crosslinking agent within a range of molar ratios of the respective components to the ethylenically unsaturated monomers, based on an amount of ethylenically unsaturated monomers added during reverse-phase suspension polymerization in each stage after the second stage. If necessary, the internal crosslinking agent may be used in reverse-phase suspension polymerization in each stage after the second stage. In a case where the internal crosslinking agent is used, reverse-phase suspension polymerization may be carried out by adding the internal crosslinking agent within a range of molar ratios of the respective components to the ethylenically unsaturated monomers based on an amount of ethylenically unsaturated monomers provided in each stage.

A temperature for the polymerization reaction varies depending on radical polymerization initiators used, and it may be 20° C. to 150° C., or may be 40° C. to 120° C., from the viewpoint that the polymerization is then promptly performed, which shortens a polymerization time, and thereby economic efficiency increases, and that polymerization heat is then easily removed, and thereby the reaction is smoothly performed. A reaction time is generally 0.5 to 4 hours. Completion of the polymerization reaction can be confirmed from, for example, stop of temperature rising in the reaction system. Accordingly, a polymer of ethylenically unsaturated monomers is generally obtained in a state of a hydrous gel polymer.

Subsequently, drying is performed to remove moisture from the obtained hydrous gel polymer. By drying, polymer particles containing the polymer of ethylenically unsaturated monomers are obtained. Examples of drying methods include a method (a) in which a hydrous gel polymer in a state of being dispersed in a hydrocarbon dispersion medium is subjected to azeotropic distillation by heating from the outside, and the hydrocarbon dispersion medium is refluxed to remove moisture; a method (b) in which a hydrous gel polymer is taken out by decantation and dried under reduced pressure; and a method (c) in which a hydrous gel polymer is separated by filtration with a filter and dried under reduced pressure. These drying methods may be carried out alone or in combination of two or more kinds thereof. The method (a) may be generally used for its simplicity in a production process. Meanwhile, the methods (b) and (c) may be used from the viewpoint of easily increasing a light transmittance of the swollen water-absorbing resin particles. One selected from the combined methods of (a) and (b), (a) and (c), and (a), (b), and (c) may be carried out from the viewpoint of compatibility between simplicity and effects.

It is possible to adjust a particle size of the water-absorbing resin particles by adjusting a rotational speed of a stirrer during the polymerization reaction or by adding a flocculating agent to the system after the polymerization reaction or at an initial time of drying. A particle size of the obtained water-absorbing resin particle can be increased by adding the flocculating agent. As the flocculating agent, an inorganic flocculating agent can be used. Examples of inorganic flocculating agents (for example, powdery inorganic flocculating agents) include silica, zeolite, bentonite, aluminum oxide, talc, titanium dioxide, kaolin, clay, and hydrotalcite. The flocculating agent may be at least one selected from the group consisting of silica, aluminum oxide, talc, and kaolin from the viewpoint of a flocculation effect.

In the reverse phase suspension polymerization, a method of adding the flocculating agent may be a method in which a flocculating agent is dispersed in a hydrocarbon dispersion medium of the same kind as that used in the polymerization, or water in advance, and then the mixture is mixed into a hydrocarbon dispersion medium containing a hydrous gel polymer under stirring.

An amount of the flocculating agent added may be 0.001 to 1 part by mass, may be 0.005 to 0.5 parts by mass, or may be 0.01 to 0.2 parts by mass, with respect to 100 parts by mass of ethylenically unsaturated monomers used in the polymerization. By setting an amount of the flocculating agent added to be within the above range, it is easy to obtain water-absorbing resin particles having a desired particle size distribution.

In the production of the water-absorbing resin particles, a surface portion of the hydrous gel polymer may be cross-linked (surface-crosslinked) using a crosslinking agent in the drying process or any of subsequent processes. By performing surface crosslinking, it is easy to control water absorption characteristics of the water-absorbing resin particles. The surface crosslinking may be performed at a timing when the hydrous gel polymer has a specific water content. A timing of the surface crosslinking may be a time point at which a water content of the hydrous gel polymer is 5% to 50% by mass, may be a time point at which a water content thereof is 10% to 40% by mass, or may be a time point at which a water content thereof is 15% to 35% by mass. A water content (% by mass) of the hydrous gel polymer is calculated by the following formula.

Water content=[$Ww/(Ww+Ws)$]×100

Ww: An amount of water of a hydrous gel polymer obtained by adding an amount of water used, as desired, upon mixing a flocculating agent, a surface crosslinking agent, and the like to an amount obtained by subtracting an amount of water extracted to the outside of the system by the drying process from an amount of water contained in an aqueous solution of monomers before polymerization in the all polymerization processes.

Ws: A solid fraction calculated from an amount of materials introduced, such as ethylenically unsaturated monomers, a crosslinking agent, and an initiator, each of which constitutes the hydrous gel polymer.

Examples of crosslinking agents (surface crosslinking agents) for performing surface crosslinking include compounds having two or more reactive functional groups. Examples of crosslinking agents include polyols such as ethylene glycol, propylene glycol, 1,4-butanediol, trimethylolpropane, glycerin, polyoxyethylene glycol, polyoxypropylene glycol, and polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether; haloepoxy compounds such as epichlorohydrin, epibromohydrin, and α-methyl epichlorohydrin; isocyanate compounds such as 2,4-tolylene diisocyanate and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol; oxazoline compounds such as 1,2-ethylenebisoxazoline; carbonate compounds such as ethylene carbonate; hydroxyalkylamide compounds such as bis[N,N-di(β-hydroxyethyl)]adipamide; and the like. The crosslinking agent may be used alone or in combination of two or more kinds thereof. The crosslinking agent may be a polyglycidyl compound, or may be at least one selected from the group consisting of (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether.

In general, a usage amount of the surface crosslinking agent may be 0.00001 to 0.02 moles, may be 0.00005 to 0.01 moles, or may be 0.0001 to 0.005 moles, with respect to 1 mole of the ethylenically unsaturated monomer used in the polymerization, from the viewpoint of exhibiting suitable water absorption characteristics by appropriately crosslinking the obtained hydrous gel polymer. In a case where an amount of the surface crosslinking agent added is within the above range, it is easy to further increase a light transmittance of the swollen water-absorbing resin particles.

It is possible to obtain polymer particles, which are a surface-crosslinked dried product, by distilling off water and the hydrocarbon dispersion medium by a known method after the surface crosslinking.

The water-absorbing resin particles according to the present embodiment may be composed of only the polymer particles, but they can further contain, for example, various additional components selected from gel stabilizers, metal chelating agents (ethylenediaminetetraacetic acid and its salts, diethylenetriaminepentaacetic acid and its salts, for example, diethylenetriaminepentaacetic acid pentasodium, and the like), flowablility improvers (lubricants), and the like. A flowablility improver may be inorganic particles such as amorphous silica. The additional components may be disposed inside the polymer particles, on a surface of the polymer particles, or both of the inside and on the surface thereof. The additional component may be flowablility improvers (lubricants), and among them, it may be inorganic particles. Examples of inorganic particles include silica particles such as amorphous silica.

The water-absorbing resin particles may contain a plurality of inorganic particles disposed on the surface of the polymer particles. The inorganic particles can be disposed on the surface of the polymer particles by, for example, mixing the polymer particles and the inorganic particles. These inorganic particles may be silica particles such as amorphous silica. In a case where the water-absorbing resin particles contain inorganic particles disposed on the surface of the polymer particles, a ratio of the inorganic particles to a mass of the polymer particles may be 0.2% by mass or more, 0.5% by mass or more, 1.0% by mass or more, or 1.5% by mass or more, and it may be 5.0% by mass or less or 3.5% by mass or less. The inorganic particles referred to herein generally have a minute size as compared with a size of the polymer particles. For example, an average particle size of the inorganic particles may be 0.1 to 50 μm, 0.5 to 30 μm, or 1 to 20 μm. The average particle size referred to herein can be a value measured by a dynamic light scattering method or a laser diffraction/scattering method.

One embodiment of the method for producing water-absorbing resin particles may further include a step of evaluating a light transmittance of the obtained water-absorbing resin particles by the method according to the above-described embodiment. For example, water-absorbing resin particles, in which a light transmittance at a wavelength of 425 nm when these water-absorbing resin particles are swollen 30 times with a physiological saline solution is equal to or more than a reference value (for example, 20%), may be sorted out. Accordingly, it is possible to more stably produce the water-absorbing resin particles capable of inhibiting liquid leakage from an absorbent article.

An absorbent according to one embodiment contains the water-absorbing resin particles according to the present embodiment. The absorbent according to the present embodiment can contain a fibrous material, and it is, for example, a mixture containing the water-absorbing resin particles and the fibrous material. The configuration of the absorbent may be, for example, a configuration in which water-absorbing resin particles and the fibrous materials are uniformly mixed, a configuration in which water-absorbing resin particles are held between fibrous materials formed in a sheet shape or a layer shape, or another configuration.

Examples of fibrous materials include finely pulverized wood pulp; cotton; cotton linter; rayon; cellulose-based fibers such as cellulose acetate; synthetic fibers such as polyamides, polyesters, and polyolefins; a mixture of these fibers; and the like. The fibrous material may be used alone or in combination of two or more kinds thereof. As the fibrous material, hydrophilic fibers can be used.

A mass proportion of the water-absorbing resin particles in the absorbent with respect to a total amount of the water-absorbing resin particles and the fibrous material may be 2% to 100% by mass, 10% to 80% by mass, or 20% to 60% by mass.

Fibers may be adhered to each other by adding an adhesive binder to the fibrous material in order to enhance shape retention properties before or during use of the absorbent. Examples of adhesive binders include thermal bonding synthetic fibers, hot-melt adhesives, and adhesive emulsions. The adhesive binder may be used alone or in combination of two or more kinds thereof.

Examples of thermal bonding synthetic fibers include full-melt binders such as polyethylene, polypropylene, and an ethylene-propylene copolymer; partial-melt binders formed of polypropylene and polyethylene in a side-by-side or core-and-sheath configuration; and the like. In the above-mentioned partial-melt binders, only a polyethylene portion can be thermal-bonded.

Examples of hot-melt adhesives include a mixture of a base polymer such as an ethylene-vinyl acetate copolymer, a styrene-isoprene-styrene block copolymer, a styrene-butadiene-styrene block copolymer, a styrene-ethylene-butylene-styrene block copolymer, a styrene-ethylene-propylene-styrene block copolymer, and an amorphous polypropylene with a viscosity imparting agent, a plasticizer, an antioxidant, or the like.

Examples of adhesive emulsions include polymers of at least one monomer selected from the group consisting of methyl methacrylate, styrene, acrylonitrile, 2-ethylhexyl acrylate, butyl acrylate, butadiene, ethylene, and vinyl acetate.

The absorbent according to the present embodiment may further contain various additives such as inorganic particles, deodorants, antibacterial agents, pigments, dyes, fragrances, and pressure sensitive adhesives, all of which are generally used in the technical field. These additives can impart various functions to the absorbent. Examples of inorganic particles include silicon dioxide, zeolite, kaolin, clay, and the like. In a case where the water-absorbing resin particles contain inorganic particles, the absorbent may further contain inorganic particles in addition to the inorganic particles in the water-absorbing resin particles.

A shape of the absorbent according to the present embodiment is not particularly limited, but it may be, for example, a sheet shape. A thickness of the absorbent (for example, a thickness of a sheet-shaped absorbent) may be, for example, 0.1 to 20 mm or 0.3 to 15 mm.

An absorbent article according to the present embodiment includes the absorbent according to the present embodiment. Examples of the absorbent article according to the present embodiment include a core wrap that retains the shape of the absorbent; a liquid-permeable sheet disposed on the outermost part on a side from which an absorption target liquid is infiltrated; a liquid-impermeable sheet disposed on the outermost part on a side opposite to the side from which the absorption target liquid is infiltrated; and the like. Examples of the absorbent article include diapers (for example, paper diapers), toilet training, incontinence pads, hygiene products (sanitary napkins, tampons, and the like), sweat pads, pet sheets, portable toilet members, animal excrement treatment materials, and the like.

FIG. 1 is a cross-sectional view showing an example of an absorbent article. An absorbent article 100 shown in FIG. 1 includes an absorbent 10, core wraps 20a and 20b, a liquid-permeable sheet 30, and a liquid-impermeable sheet 40. In the absorbent article 100, the liquid-impermeable sheet 40, the core wrap 20b, the absorbent 10, the core wrap 20a, and the liquid-permeable sheet 30 are laminated in this order. In FIG. 1, there is a portion shown to be a gap between the members, but the members may be in close contact with each other without the gap.

The absorbent 10 has water-absorbing resin particles 10a according to the present embodiment and a fiber layer 10b containing a fibrous material. The water-absorbing resin particles 10a are dispersed in the fiber layer 10b.

Liquid absorption performances of the absorbent article 100 are also affected by water absorption performances of the water-absorbing resin particles 10a used. Accordingly, for the water-absorbing resin particles 10a, water-absorbing resin particles, in which water absorption performances such as a light transmittance, a liquid absorption capacity (represented by indexes such as a water retention capacity, and a water absorption capacity under a load), and a water absorption speed; a mass average particle size; and the like of the water-absorbing resin particles 10a are within suitable ranges, may be selected in consideration of the configuration of each of the components of the absorbent article 100, and the like.

A content of the water-absorbing resin particles 10a may be 100 to 1,000 g per square meter of the absorbent 10 (that is, 100 to 1,000 $g/m^2$), may be 150 to 800 $g/m^2$, or may be 200 to 700 $g/m^2$, from the viewpoint that sufficient liquid absorption performances can then be more easily obtained when the absorbent 10 is used for the absorbent article 100. A content of the water-absorbing resin particles 10a may be 100 $g/m^2$ or more from the viewpoint of exhibiting sufficient liquid absorption performances as the absorbent article 100 and thereby inhibiting, particularly liquid leakage. A content of the water-absorbing resin particles 10a may be 1,000 $g/m^2$ or less from the viewpoint of inhibiting occurrence of a gel blocking phenomenon, and thereby exhibiting a diffusion performance of a liquid as the absorbent article 100 and further improving a permeation speed of the liquid.

A content of the fibrous material may be 50 to 800 g per square meter of the absorbent 10 (that is, 50 to 800 g/m$^2$), may be 100 to 600 g/m$^2$, or may be 150 to 500 g/m$^2$, from the viewpoint that sufficient liquid absorption performances are then obtained when the absorbent 10 is used for the absorbent article 100. A content of the fibrous material may be 50 g or more per square meter of the absorbent 10 (that is, 50 g/m$^2$ or more) from the viewpoint of exhibiting sufficient liquid absorption performances as the absorbent article 100, and thereby particularly inhibiting occurrence of a gel blocking phenomenon to improve a diffusion performance of a liquid, and increasing strength of the absorbent 10 after it absorbs a liquid. A content of the fibrous material may be 800 g or less per square meter of the absorbent 10 (that is, 800 g/m$^2$ or less) from the viewpoint of particularly inhibiting reversion after liquid absorption.

The core wrap 20a is disposed on one surface side of the absorbent 10 (an upper side of the absorbent 10 in FIG. 1) in a state of being in contact with the absorbent 10. That is, the core wrap 20a covers at least the surface side of the absorbent 10 in contact with the liquid-permeable sheet 30. The core wrap 20b is disposed on the other surface side of the absorbent 10 (a lower side of the absorbent 10 in FIG. 1) in a state of being in contact with the absorbent 10. That is, the core wrap 20b covers at least the surface side of the absorbent 10 in contact with the liquid-impermeable sheet 40. The absorbent 10 is disposed between the core wrap 20a and the core wrap 20b. The core wrap 20a and the core wrap 20b each have, for example, a main surface having the same size as that of the absorbent 10. The shape of the absorbent 10 is maintained (that is, shape retainability can be enhanced) in the absorbent article 100 having the core wraps 20a and 20b, and thereby fall off and flow of the water-absorbing resin particles 10a and the like constituting the absorbent 10 are prevented or inhibited.

Examples of the core wraps 20a and 20b include non-woven fabrics, woven fabrics, synthetic resin films having liquid permeation holes, net-like sheets having a mesh, and the like. The core wraps 20a and 20b may be tissues obtained by wet-type molding pulverized pulp from the viewpoint of economic efficiency.

The liquid-permeable sheet 30 is disposed on the outermost part on a side from which an absorption target liquid is infiltrated. The liquid-permeable sheet 30 is disposed on the core wrap 20a in a state of being in contact with the core wrap 20a. The liquid-permeable sheet 30 has, for example, a main surface wider than the main surface of the absorbent 10, and an outer edge of the liquid-permeable sheet 30 extends around the absorbent 10 and the core wraps 20a and 20b.

The liquid-permeable sheet 30 may be a sheet formed of resin or fiber generally used in the technical field. From the viewpoint of liquid permeability, flexibility, and strength when the liquid-permeable sheet 30 is used in an absorbent article, the liquid-permeable sheet 30 may contain, for example, synthetic resins such as polyolefins such as polyethylene (PE) and polypropylene (PP); polyesters such as polyethylene terephthalate (PET), polytrimethylene terephthalate (PTT), and polyethylene naphthalate (PEN); polyamides such as nylon; and rayon, or synthetic fibers containing these synthetic resins, or the liquid-permeable sheet 30 may be natural fibers including cotton, silk, hemp, or pulp (cellulose). The liquid-permeable sheet 30 may contain synthetic fibers from the viewpoint of increasing strength of the liquid-permeable sheet 30. Synthetic fibers may be particularly polyolefin fibers, polyester fibers, or a combination thereof. These materials may be used alone or in combination of two or more materials.

The liquid-permeable sheet 30 may be a non-woven fabric, a porous sheet, or a combination thereof. Non-woven fabric is a sheet in which fibers are entwined instead of being woven. The non-woven fabric may be a non-woven fabric (short-fiber non-woven fabric) composed of short fibers (that is, staples), or may be a non-woven fabric (long-fiber non-woven fabric) composed of long fibers (that is, filaments). In general, staples may have a fiber length of several hundred millimeters or shorter, but its length is not limited thereto.

The liquid-permeable sheet 30 may be thermal bonded non-woven fabrics, air through non-woven fabrics, resin bonded non-woven fabrics, spunbond non-woven fabrics, melt-blown non-woven fabrics, airlaid non-woven fabrics, spunlace non-woven fabrics, point-bonded non-woven fabrics, or a laminate of two or more of non-woven fabrics selected from these non-woven fabrics. These non-woven fabrics can be, for example, non-woven fabrics formed of the above-mentioned synthetic fibers or natural fibers. The laminate of two or more of non-woven fabrics may be, for example, a spunbond/melt-blown/spunbond non-woven fabric that is a composite non-woven fabric having spunbond non-woven fabric, melt-blown non-woven fabric, and spunbond non-woven fabric, which are laminated in this order. The liquid-permeable sheet 30 may be a thermal bonded non-woven fabric, an air through non-woven fabric, a spunbond non-woven fabric, or a spunbond/melt-blown/spunbond non-woven fabric, from the viewpoint of inhibiting liquid leakage.

It is desirable that a non-woven fabric used as the liquid-permeable sheet 30 have appropriate hydrophilicity from the viewpoint of liquid absorption performances of the absorbent article. From this viewpoint, the liquid-permeable sheet 30 may be a non-woven fabric having a hydrophilicity of 5 to 200 as measured according to a measurement method of Pulp and Paper Test Method No. 68 (2000) by the Japan Technical Association of Pulp and Paper Industry. The hydrophilicity of the non-woven fabric may be 10 to 150. For details of Pulp and Paper Test Method No. 68, for example, WO2011/086843 can be referred to.

The hydrophilic non-woven fabric as described above may be formed of fibers, such as rayon fibers, showing appropriate hydrophilicity, or may be formed of fibers obtained by hydrophilizing hydrophobic chemical fibers such as polyolefin fibers and polyester fibers. Examples of methods of obtaining a non-woven fabric containing hydrophobic chemical fibers that have been hydrophilized include a method of obtaining a non-woven fabric by a spunbond technique using a mixture in which a hydrophilizing agent is added to hydrophobic chemical fibers, a method of using a hydrophilizing agent when producing a spunbond non-woven fabric from hydrophobic chemical fibers, and a method of impregnating a spunbond non-woven fabric obtained by using hydrophobic chemical fibers with a hydrophilizing agent. As the hydrophilizing agent, the following examples are used: anionic surfactants such as aliphatic sulfonic acid salts and higher alcohol sulfuric acid ester salts; cationic surfactants such as quaternary ammonium salts; nonionic surfactants such as polyethylene glycol fatty acid esters, polyglycerin fatty acid esters, and sorbitan fatty acid esters; silicone surfactants such as polyoxyalkylene-modified silicone; stain release agents formed of polyester-based, polyamide-based, acrylic-based, or urethane-based resin; and the like.

The liquid-permeable sheet 30 may be a non-woven fabric that is moderately bulky and has a large fabric weight per unit area from the viewpoint of imparting favorable liquid permeability, flexibility, strength, and cushioning properties to an absorbent article, and from the viewpoint of accelerating a liquid permeation speed of an absorbent article. A fabric weight per unit area of the non-woven fabric used for the liquid-permeable sheet 30 may be 5 to 200 g/m$^2$, may be 8 to 150 g/m$^2$, or may be 10 to 100 g/m$^2$. A thickness of the non-woven fabric used for the liquid-permeable sheet 30 may be 20 to 1,400 μm, may be 50 to 1,200 μm, or may be 80 to 1,000 μm.

In the absorbent article 100 having the core wrap 20a, the core wrap 20a may be adhered to the liquid-permeable sheet 30. In this case, a liquid is more smoothly guided to the absorbent 10, and thereby it is possible to obtain the absorbent article 100 having a further better effect of inhibiting liquid leakage. The core wrap 20a may be adhered to at least the liquid-permeable sheet 30, or the core wrap 20a may be adhered to the absorbent 10 in addition to being adhered to the liquid-permeable sheet 30.

In the absorbent article in which the absorbent is disposed to be in contact with the liquid-permeable sheet, the absorbent may be adhered to the liquid-permeable sheet. In this case, a liquid is more smoothly guided to the absorbent 10, and thereby it is possible to obtain the absorbent article 100 having a further better effect of inhibiting liquid leakage.

Examples of methods of adhering the absorbent 10 and/or the core wrap 20a to the liquid-permeable sheet include a method of adhering them by applying the hot-melt adhesive to the liquid-permeable sheet 30 in a vertical stripe shape, a spiral shape, or the like at predetermined intervals in a width direction; a method of adhering them using a water-soluble binder selected from starch, carboxymethyl cellulose, polyvinyl alcohol, polyvinylpyrrolidone, and other water-soluble polymers; and the like. Furthermore, a method of adhering them by thermal bonding may be adopted in a case where the absorbent 10 contains the thermal bonding synthetic fibers.

The liquid-impermeable sheet 40 is disposed on the outermost part on a side opposite to the liquid-permeable sheet 30, in the absorbent article 100. The liquid-impermeable sheet 40 is disposed below the core wrap 20b in a state of being in contact with the core wrap 20b. The liquid-impermeable sheet 40 has, for example, a main surface wider than the main surface of the absorbent 10, and an outer edge of the liquid-impermeable sheet 40 extends around the absorbent 10 and the core wraps 20a and 20b. The liquid-impermeable sheet 40 prevents a liquid absorbed by the absorbent 10 from leaking to the outside from the liquid-impermeable sheet 40 side.

Examples of the liquid-impermeable sheet 40 include sheets made of synthetic resins such as polyethylene, polypropylene, and polyvinyl chloride; sheets made of non-woven fabric such as a spunbond/melt-blown/spunbond (SMS) non-woven fabric in which a water-resistant melt blown non-woven fabric is sandwiched between high-strength spunbond non-woven fabrics; sheets made of a composite material of these synthetic resins and non-woven fabric (for example, spunbond non-woven fabric and spunlace non-woven fabric); and the like. The liquid-impermeable sheet 40 may have breathability from the viewpoint that dampness generated when wearing the absorbent article is then reduced, and thereby discomfort to a wearer can be reduced. As the liquid-impermeable sheet 40, it is possible to use a sheet made of a synthetic resin mainly composed of a low density polyethylene (LDPE) resin. The liquid-impermeable sheet 40 may be, for example, a sheet made of a synthetic resin and having a fabric weight per unit area of 10 to 50 g/m$^2$ from the viewpoint of ensuring flexibility so as not to impair a sensation of wearing the absorbent article.

A magnitude relationship between the absorbent 10, the core wraps 20a, and 20b, the liquid-permeable sheet 30, and the liquid-impermeable sheet 40 is not particularly limited, and it is appropriately adjusted according to usage applications and the like of the absorbent article. Furthermore, a method of retaining the shape of the absorbent 10 using the core wraps 20a and 20b is not particularly limited. The absorbent may be wrapped with a plurality of the core wraps as shown in FIG. 1, or the absorbent may be wrapped with one core wrap.

According to the present embodiment, it is possible to provide a method of absorbing a liquid using the water-absorbing resin particles, absorbent, or absorbent article according to the present embodiment. The method of absorbing a liquid according to the present embodiment includes a step of bringing an absorption target liquid into contact with the water-absorbing resin particles, absorbent, or absorbent article according to the present embodiment.

The present invention can also be regarded as a method for evaluating liquid leakage properties of water-absorbing resin particles which is a method in which an effect of inhibiting liquid leakage of the water-absorbing resin particles is evaluated to be high in a case where a light transmittance of the water-absorbing resin particles at a wavelength of 425 nm when these particles are swollen 30 times with a physiological saline solution is 20% or more.

EXAMPLES

Hereinafter, the present invention will be described in more detail with reference to examples, but the present invention is not limited to these examples.

<Production of Water-Absorbing Resin Particles>

[Production of Water-Absorbing Resin Particles of Example 1]

First-Stage Polymerization Reaction

A cylindrical round-bottomed separable flask was prepared, which had an inner diameter of 11 cm and an internal capacity of 2 L, and was equipped with a reflux condenser, a dropping funnel, a nitrogen gas introduction tube, and as a stirrer, a stirring blade having four inclined paddle blades, each having a blade diameter of 5 cm, in a two-tier manner. 293 g of n-heptane was weighed into this flask, and 0.736 g of a maleic anhydride-modified ethylene-propylene copolymer (HI-WAX 1105A, manufactured by Mitsui Chemicals, Inc.) as a polymeric dispersant was put thereinto. The reaction solution in the flask was heated to 80° C. while being stirred to dissolve the polymeric dispersant in the n-heptane. Thereafter, the reaction solution was cooled to 50° C.

92.0 g (1.03 moles) of an aqueous solution of acrylic acid at a concentration of 80.5% by mass was put into a beaker with an internal capacity of 300 mL. 147.7 g of an aqueous solution of sodium hydroxide at a concentration of 20.9% by mass was added dropwise into the aqueous solution of acrylic acid while cooling the beaker from the outside, and thereby 75 mol % of acrylic acid was neutralized. Then, 0.092 g of hydroxylethyl cellulose (HEC AW-15F, manufactured by Sumitomo Seika Chemicals Co., Ltd.) as a thickener, 0.074 g (0.272 mmol) of potassium persulfate as a radical polymerization initiator, and 0.0156 g (0.090 mmol) of ethylene glycol diglycidyl ether as an internal crosslinking agent were dissolved in the aqueous solution of acrylic acid. Thereby, a first-stage aqueous solution of monomers was prepared.

The first-stage aqueous solution of monomers was added into the above-mentioned reaction solution in the separable flask, and the reaction solution was stirred for 10 minutes. Then, a surfactant solution containing 6.62 g of n-heptane and 0.736 g of sucrose stearic acid ester (HLB: 3, manufactured by Mitsubishi-Chemical Foods Corporation, RYOTO Sugar Ester S-370) was added into the reaction solution. While stirring the reaction solution at 450 rpm as a rotational speed of the stirring blade, the inside of the system was sufficiently replaced with nitrogen. Thereafter, a polymerization reaction was caused to proceed for 60 minutes while heating the separable flask in a water bath at 70° C. By this polymerization reaction, a first-stage polymerization slurry liquid containing a hydrous gel polymer was obtained.

Second-Stage Polymerization Reaction 128.8 g (1.43 moles) of an aqueous solution of acrylic acid at a concentration of 80.5% by mass was put into a beaker with an internal capacity of 500 mL. 159.0 g of an aqueous solution of sodium hydroxide at a concentration of 27% by mass was added dropwise into the aqueous solution of acrylic acid while cooling the beaker from the outside, and thereby 75 mol % of acrylic acid was neutralized. Then, 0.090 g (0.334 mmol) of potassium persulfate, and 0.0129 g (0.074 mmol) of ethylene glycol diglycidyl ether as an internal crosslinking agent were dissolved in the aqueous solution of acrylic acid. Thereby, a second-stage aqueous solution of monomers was prepared.

While stirring the first-stage polymerization slurry liquid in the separable flask at 1,000 rpm as a rotational speed of the stirring blade, the separable flask was cooled to 28.5° C. Then, a total amount of the second-stage aqueous solution of monomers was added thereinto, and then the inside of the system was replaced with nitrogen over 30 minutes. Thereafter, a polymerization reaction was caused to proceed for 60 minutes while heating the separable flask in a water bath at 70° C.

0.265 g of an aqueous solution of diethylenetriaminepentaacetic acid pentasodium at a concentration of 45% by mass was added into the reaction solution containing the hydrous gel polymer under stirring. Thereafter, the flask was immersed in an oil bath set to 125° C., and 258.9 g of water was extracted out of the system by azeotropic distillation with n-heptane and water. Thereafter, 4.42 g (0.507 mmol) of an aqueous solution of ethylene glycol diglycidyl ether at a concentration of 2% by mass as a surface crosslinking agent was added into the reaction solution, and a crosslinking reaction by a surface crosslinking agent was caused to proceed at 83° C. for 2 hours.

Immediately after the surface crosslinking reaction, the n-heptane phase was separated from the reaction solution by filtration through a sieve having an aperture of 38 μm, and thereby a highly water-absorbing resin hydrous product was obtained. This highly water-absorbing resin hydrous product was dried in a vacuum drier set at 90° C. under heating and decompression of 0.006 MPa. Thereby, a dried product of polymer particles was obtained.

The obtained polymer particles (dried product) were passed through a sieve having an aperture of 850 μm. Thereafter, 0.5% by mass of amorphous silica (Oriental Silicas Corporation, Tokusil NP-S) with respect to a mass of the polymer particles was mixed with the polymer particles, and thereby 231.5 g of water-absorbing resin particles containing the amorphous silica was obtained. A median particle size of the water-absorbing resin particles was 364 μm, and a water absorption speed of the water-absorbing resin particles for a physiological saline solution was 36 seconds.

[Production of Water-Absorbing Resin Particles of Example 2]

A dried product of water-absorbing resin particles was obtained in the same procedure as in Example 1 except that, in the first-stage polymerization reaction, a radical polymerization initiator was changed to 0.092 g (0.339 mmol) of 2,2'-azobis(2-amidinopropane) dihydrochloride and 0.018 g (0.068 mmol) of potassium persulfate, an internal crosslinking agent was changed to 0.0101 g (0.058 mmol) of ethylene glycol diglycidyl ether, and a rotational speed of the stirring blade was changed to 550 rpm; in the second-stage polymerization reaction, a radical initiator was changed to 0.129 g (0.475 mmol) of 2,2'-azobis(2-amidinopropane) dihydrochloride and 0.026 g (0.095 mmol) of potassium persulfate, an internal crosslinking agent was changed to 0.0116 g (0.067 mmol) of ethylene glycol diglycidyl ether, and a first-stage polymerization slurry was cooled to 25° C.; and an amount of water extracted from a reaction solution containing a hydrous gel polymer by azeotropic distillation was changed to 239.9 g.

0.2% by mass of amorphous silica (Oriental Silicas Corporation, Tokusil NP-S) with respect to a mass of the polymer particles (dried product) was mixed with the polymer particles, and thereby 231.5 g of water-absorbing resin particles containing the amorphous silica was obtained. A median particle size of the water-absorbing resin particles was 384 μm, and a water absorption speed of the water-absorbing resin particles for a physiological saline solution was 38 seconds.

[Production of Water-Absorbing Resin Particles of Example 3]

A cylindrical round-bottomed separable flask was prepared, which had an inner diameter of 11 cm and a capacity of 2 L, and was equipped with a reflux condenser, a dropping funnel, a nitrogen gas introduction tube, and as a stirrer, a stirring blade having four inclined paddle blades, each having a blade diameter of 5 cm, in a two-tier manner. 281 g of cyclohexane was weighed into this flask, and 0.564 g of ethyl cellulose (manufactured by Ashland, trade name: Aqualon N100) was put thereinto. While stirring the mixture at 700 rpm as a rotational speed of the stirrer, nitrogen gas was blown into the system to expel dissolved oxygen. The flask was immersed in a water bath at 80° C. and heated to 75° C.

Meanwhile, 92.0 g (1.28 moles) of 100% by mass acrylic acid as an ethylenically unsaturated monomer was weighed into a beaker with an internal capacity of 300 mL, and 142.0 g of an aqueous solution of 27% by mass sodium hydroxide was added dropwise thereto while cooling the beaker from the outside to perform neutralization to 75 mol %. Thereafter, a solution, obtained by dissolving 0.184 g (0.681 mmol) of potassium persulfate as a radical polymerization initiator in 14.8 g of water, was added into the reaction solution and dissolved. Thereafter, nitrogen gas was blown into the system to remove oxygen remaining in the aqueous solution, and thereby an aqueous solution of monomers was prepared.

The prepared aqueous solution of monomers was added dropwise into the above separable flask system using a tube pump over 1 hour to carry out a polymerization reaction. After the polymerization, the flask was immersed in an oil bath set to 125° C. while stirring at 1,000 rpm as a rotational speed of the stirrer, and 107.2 g of water was extracted out of the system while cyclohexane was refluxed by azeotropic distillation with cyclohexane and water.

Thereafter, 0.036 g (0.176 mmol) of polyglycerol polyglycidyl ether (manufactured by Nagase Kasei Kogyo Co., Ltd., trade name DENACOL EX-512) was added and dissolved in 3.61 g of water as a surface crosslinking agent in the flask. The reaction was carried out at 75° C. to 80° C. for 1 hour while heating the flask in an oil bath. Immediately after the reaction, the cyclohexane phase was separated by filtration through a sieve having an aperture of 38 μm, and thereby a highly water-absorbing resin hydrous product was obtained.

This highly water-absorbing resin hydrous product was dried in a vacuum drier set at 90° C. under heating and decompression of 0.006 MPa. Thereby, polymer particles were obtained. These particles were passed through a sieve having an aperture of 850 μm, and 0.5% by mass of amorphous silica (Oriental Silicas Corporation, Tokusil NP-S) with respect to a mass of the polymer particles (dried product) was mixed with the polymer particles. Thereby, 105.1 g of water-absorbing resin particles containing the amorphous silica was obtained. A median particle size of the water-absorbing resin particles was 310 μm.

[Production of Water-Absorbing Resin Particles of Comparative Example 1]

A dried product of polymer particles was obtained in the same procedure as in Example 1 except that, in the first-stage polymerization reaction, an internal crosslinking agent was changed to 0.010 g (0.057 mmol) of ethylene glycol diglycidyl ether, and a rotational speed of the stirring blade was changed to 550 rpm; in the second-stage polymerization reaction, an internal crosslinking agent was changed to 0.0116 g (0.067 mmol) of ethylene glycol diglycidyl ether, and a temperature for cooling a first-stage polymerization slurry was changed to 25° C.; an amount of water extracted from a reaction solution containing a hydrous gel polymer by azeotropic distillation was changed to 256.1 g; and n-heptane was evaporated to dryness at 125° C. instead of separating the n-heptane phase by filtration.

0.1% by mass of amorphous silica (Oriental Silicas Corporation, Tokusil NP-S) with respect to a mass of the polymer particles (dried product) was mixed with the polymer particles, and thereby 230.8 g of water-absorbing resin particles containing the amorphous silica was obtained. A median particle size of the water-absorbing resin particles was 349 μm, and a water absorption speed of the water-absorbing resin particles for a physiological saline solution was 37 seconds.

[Production of Water-Absorbing Resin Particles of Comparative Example 2]

A dried product of polymer particles was obtained in the same procedure as in Example 1 except that, in the first-stage polymerization reaction, a radical polymerization initiator was changed to 0.092 g (0.339 mmol) of 2,2'-azobis(2-amidinopropane) dihydrochloride and 0.018 g (0.068 mmol) of potassium persulfate, an internal crosslinking agent was changed to 0.0046 g (0.026 mmol), and a rotational speed of the stirring blade was changed to 550 rpm; in the second-stage polymerization reaction, a radical initiator was changed to 0.129 g (0.475 mmol) of 2,2'-azobis(2-amidinopropane) dihydrochloride and 0.026 g (0.095 mmol) of potassium persulfate, an internal crosslinking agent was changed to 0.0116 g (0.067 mmol) of ethylene glycol diglycidyl ether, and a temperature for cooling a first-stage polymerization slurry was changed to 25° C.; an amount of water extracted from a reaction solution containing a hydrous gel polymer by azeotropic distillation was changed to 210.0 g; and n-heptane was evaporated to dryness at 125° C. instead of separating the n-heptane phase by filtration.

0.2% by mass of amorphous silica (Oriental Silicas Corporation, Tokusil NP-S) with respect to a mass of the polymer particles (dried product) was mixed with the polymer particles, and thereby 229.6 g of water-absorbing resin particles containing the amorphous silica was obtained. A median particle size of the water-absorbing resin particles was 356 μm, and a water absorption speed of the water-absorbing resin particles for a physiological saline solution was 56 seconds.

[Production of Water-Absorbing Resin Particles of Comparative Example 3]

A dried product of polymer particles was obtained in the same procedure as in Example 1 except that, in the first-stage polymerization reaction, a radical polymerization initiator was changed to 0.092 g (0.339 mmol) of 2,2'-azobis(2-amidinopropane) dihydrochloride and 0.018 g (0.068 mmol) of potassium persulfate, an internal crosslinking agent was changed to 0.0046 g (0.026 mmol) of ethylene glycol diglycidyl ether, and a rotational speed of the stirring blade was changed to 550 rpm; in the second-stage polymerization reaction, a radical initiator was changed to 0.129 g (0.475 mmol) of 2,2'-azobis(2-amidinopropane) dihydrochloride and 0.026 g (0.095 mmol) of potassium persulfate, an internal crosslinking agent was changed to 0.0116 g (0.067 mmol) of ethylene glycol diglycidyl ether, and a temperature for cooling a first-stage polymerization slurry was changed to 25° C.; an amount of water extracted from a reaction solution containing a hydrous gel polymer by azeotropic distillation was changed to 234.2 g; and n-heptane was evaporated to dryness at 125° C. instead of separating the n-heptane phase by filtration.

0.2% by mass of amorphous silica (Oriental Silicas Corporation, Tokusil NP-S) with respect to a mass of the polymer particles (dried product) was mixed with the polymer particles, and thereby 229.6 g of water-absorbing resin particles containing the amorphous silica was obtained. A median particle size of the water-absorbing resin particles was 355 μm, and a water absorption speed of the water-absorbing resin particles for a physiological saline solution was 48 seconds.

<Evaluation of Water-Absorbing Resin Particles>

Table 1 shows measurement results of water retention capacities, for a physiological saline solution, of the water-absorbing resin particles of the examples and the comparative examples, and light transmittances thereof measured by a method described below.

TABLE 1

| | Performance of water-absorbing resin particles | |
|---|---|---|
| Water-absorbing resin particles | Water retention capacity [g/g] | Light transmittance (%) when swollen 30 times Physiological saline solution |
| Example 1 | 35 | 52.1 |
| Example 2 | 41 | 55.9 |
| Example 3 | 41 | 73.0 |
| Comparative Example 1 | 41 | 13.8 |
| Comparative Example 2 | 34 | 10.1 |
| Comparative Example 3 | 51 | 13.4 |

<Measurement of Light Transmittance>

The following instruments and devices were used to measure a light transmittance of the swollen water-absorbing resin particles.

Quartz cell (manufactured by Tosoh Quartz Corporation: 10 [mm]×10 [mm]×45 [mm])

Centrifuge (manufactured by KOKUSAN Co., Ltd.: H-36)

UV measuring device: UV-VIS SPECTROPHOTOMETER (manufactured by Shimadzu Corporation: UV-1850)

A light transmittance was measured according to the following procedure. 0.1 g of the water-absorbing resin particles was put into a quartz cell, and 3 g of an aqueous solution of 0.9% by mass sodium chloride (physiological saline solution) prepared at 25° C. was injected thereinto using a macropipette. The mixture was left to stand for 30 minutes so that the water-absorbing resin particles absorbed the solution, and thereby, a swollen gel layer was produced. Thereafter, defoaming was performed for 10 minutes at a rotational speed of 200 rpm using a centrifuge, and then a light transmittance [%] of the swollen gel layer in the quartz cell at 425 nm was measured using the UV measuring device.

<Measurement of Water Retention Capacity for Physiological Saline Solution>

A cotton bag (cotton broadcloth No. 60, 100 mm in width×200 mm in length) into which 2.0 g of the water-absorbing resin particles had been weighed was placed in a beaker having a capacity of 500 mL. 500 g of an aqueous solution of 0.9% by mass sodium chloride (physiological saline solution) was poured into the cotton bag containing the water-absorbing resin particles at once so that a lump could not be produced. The upper part of the cotton bag was bound with a rubber band and left to stand for 30 minutes, and thereby the water-absorbing resin particles were swollen. The cotton bag after an elapse of 30 minutes was dehydrated for 1 minute using a dehydrator (manufactured by KOKUSAN Co., Ltd., product number: H-122) which had been set at a centrifugal force of 167 G, and a mass Wa (g) of the dehydrated cotton bag containing the swollen gel was measured. By performing the same operation without addition of the water-absorbing resin particles, a mass Wb (g) of an empty cotton bag upon moisturizing was measured, and a water retention capacity for a physiological saline solution was calculated by the following formula.

Water retention capacity for physiological saline solution (g/g)=[$Wa-Wb$]/2.0

<Median Particle Size (Particle Size Distribution)>

50 g of the water-absorbing resin particles was used for measuring a median particle size (particle size distribution).

JIS standard sieves were combined in the following order from the top: a sieve having an aperture of 850 μm, a sieve having an aperture of 500 μm, a sieve having an aperture of 425 μm, a sieve having an aperture of 300 μm, a sieve having an aperture of 250 μm, a sieve having an aperture of 180 μm, a sieve having an aperture of 150 μm, and a receiving tray.

The water-absorbing resin particles were fed to the topmost sieve among the combination of the sieves, shaken for 20 minutes using a Ro-Tap shaker, and thereby classified. After the classification, a mass of the water-absorbing resin particles remaining on each of the sieves was calculated as a mass percentage with respect to a total amount to determine a particle size distribution. By integrating values on the sieves in descending order of the particle sizes with regard to the particle size distribution, a relationship between the aperture of the sieve and the integrated value of mass percentages of the water-absorbing resin particles remaining on the sieve was plotted on a log-probability paper. The plotted points on the probability paper were connected with straight lines, and a particle size corresponding to 50% by mass of the integrated mass percentage was taken as a median particle size.

A presence proportion of water-absorbing resin particles having a particle size of more than 250 μm and equal to or less than 850 μm is a sum of proportions of water-absorbing resin particles remaining on the sieves respectively having apertures of 500 μm, 425 μm, 300 μm, and 250 μm. Similarly, a presence proportion of water-absorbing resin particles having a particle size of 250 μm or less is a numerical value obtained by adding up all proportions of water-absorbing resin particles remaining on the sieves respectively having apertures of 180 μm and 150 μm and the receiving tray.

<Measurement of Water Absorption Speed for Physiological Saline Solution>

50±0.1 g of an aqueous solution of 0.9% NaCl, which had been adjusted to a temperature of 25±0.2° C. in a thermostatic water bath, was weighed into a 100 mL beaker and stirred with a magnetic stirrer bar (8 mmφ×30 mm, without a ring) to generate a vortex at a rotational speed of 600 rpm. 2.0±0.002 g of the water-absorbing resin particles was added into the aqueous solution of 0.9% NaCl at once, and a time (sec) until the vortex on the liquid surface became calm after the addition of the water-absorbing resin particles was measured. The time was taken as a water absorption speed of the water-absorbing resin particles for a physiological saline solution. This water absorption speed is also expressed as a water absorption speed by a Vortex method, or a vortex time.

<Preparation of Artificial Urine>

A solution was prepared by blending and dissolving components in ion exchange water so that inorganic salts were present as shown below. A small amount of Blue No. 1 was further blended therein, and thereby artificial urine was prepared. The following concentrations are concentrations based on a total mass of the artificial urine.

Composition of Artificial Urine

NaCl: 0.780% by mass
$CaCl_2$: 0.022% by mass
$MgSO_4$: 0.038% by mass
Blue No. 1: 0.002% by mass <Inclination Leakage Test>

Liquid leakage properties of the water-absorbing resin particles were evaluated by the following procedures i), ii), iii), iv) and v).

i) A strip-shaped adhesive tape (manufactured by DIA-TEX Co., Ltd., Piolan tape) having a length of 15 cm and a width of 5 cm was put on a laboratory table such that an adhesive surface faced up, and 3.0 g of the water-absorbing resin particles was evenly dispersed onto this adhesive surface. A stainless steel roller (mass 4.0 kg, diameter 10.5 cm, width 6.0 cm) was placed on the upper part of the dispersed water-absorbing resin particles, and this roller was caused to reciprocate three times between both ends of the adhesive tape in a longitudinal direction. Accordingly, a water-absorbing layer formed of the water-absorbing resin particles was formed on the adhesive surface of the adhesive tape.

ii) The adhesive tape was stood vertically to remove excess water-absorbing resin particles from the water-absorbing layer. The roller was placed on the water-absorbing layer again and caused to reciprocate three times between both ends of the adhesive tape in the longitudinal direction.

iii) In a room at a temperature of 25±2° C., an acrylic resin plate having a rectangular flat main surface with a length of 30 cm and a width of 55 cm was fixed such that its width direction was parallel to the horizontal plane, and an angle between its main surface and the horizontal plane was 30 degrees. The adhesive tape on which the water-absorbing layer was formed was bonded to the main surface of the fixed acrylic plate such that the water-absorbing layer was exposed and in a direction in which the longitudinal direction of the adhesive tape was perpendicular to the width direction of the acrylic resin plate.

iv) Using a micropipette (PIPETMAN Neo P1000N manufactured by M&S Instruments Inc.), 0.25 mL of a test solution at a liquid temperature of 25° C. was entirely injected within 1 second into a position about 1 cm from the upper end of the water-absorbing layer, from a height of about 1 cm from the surface.

v) 30 seconds after the start of the injection of the test solution, a maximum value of a moving distance of the test solution injected into the water-absorbing layer was read and recorded as a diffusion distance D. The diffusion distance D is a distance on the main surface connecting a dropping point (injection point) and the longest reaching point with a straight line in a direction perpendicular to the horizontal plane of the short side of the acrylic resin plate. When the diffusion distance D was 14 cm or longer, liquid leakage occurred.

TABLE 2

| Example Comparative Example | Inclination leakage test [cm] |
|---|---|
| Example 1 | 8.0 |
| Example 2 | 7.5 |
| Example 3 | 8.0 |
| Comparative Example 1 | 14 or more |
| Comparative Example 2 | 14 or more |
| Comparative Example 3 | 14 or more |

It was shown that liquid leakage can be inhibited by the water-absorbing resin particles in which a light transmittance at a wavelength of 425 nm when these particles are swollen 30 times with a physiological saline solution is equal to or more than a predetermined value.

<Production of Absorbent and Absorbent Article>

[Production of Absorbent Article Containing Water-Absorbing Resin Particles of Example 1]

10 g of the water-absorbing resin particles of Example 1 and 9.5 g of pulverized pulp were uniformly mixed by air papermaking using an air flow type mixer (Padformer manufactured by OTEC Co., Ltd.), and thereby a sheet-shaped absorbent having a size of 12 cm×32 cm was produced. The absorbent was disposed on a tissue paper (core wrap) having a basis weight of 16 g/m². A tissue paper (core wrap), and an air through non-woven fabric (liquid-permeable sheet), which is a short-fiber non-woven fabric, were laminated on the absorbent in this order. A load of 588 kPa was applied to this laminate for 30 seconds. Furthermore, a polyethylene liquid-impermeable sheet having a size of 12 cm×32 cm was bonded to a surface on the side opposite to the air through non-woven fabric, and thereby an absorbent article containing the water-absorbing resin particles of Example 1 was produced. A fabric weight per unit area of the air through non-woven fabric used was 17 g/m².

[Production of Absorbent Article Containing Water-Absorbing Resin Particles of Example 2]

An absorbent article containing the water-absorbing resin particles of Example 2 was produced in the same manner as in Example 1 except that the water-absorbing resin particles were changed to the water-absorbing resin particles of Example 2.

[Production of Absorbent Articles Containing Water-Absorbing Resin Particles of Comparative Examples 1 to 3]

Absorbent articles respectively containing the water-absorbing resin particles of Comparative Examples 1 to 3 were produced in the same manner as in Example 1 except that the water-absorbing resin particles were changed to the water-absorbing resin particles of Comparative Examples 1 to 3.

In the absorbent articles of the examples and the comparative examples, a basis weight of the water-absorbing resin particles was 280 g/m², and a basis weight of the pulverized pulp (hydrophilic fibers) was 260 g/m².

<Slope Absorption Test>

Figure 2:
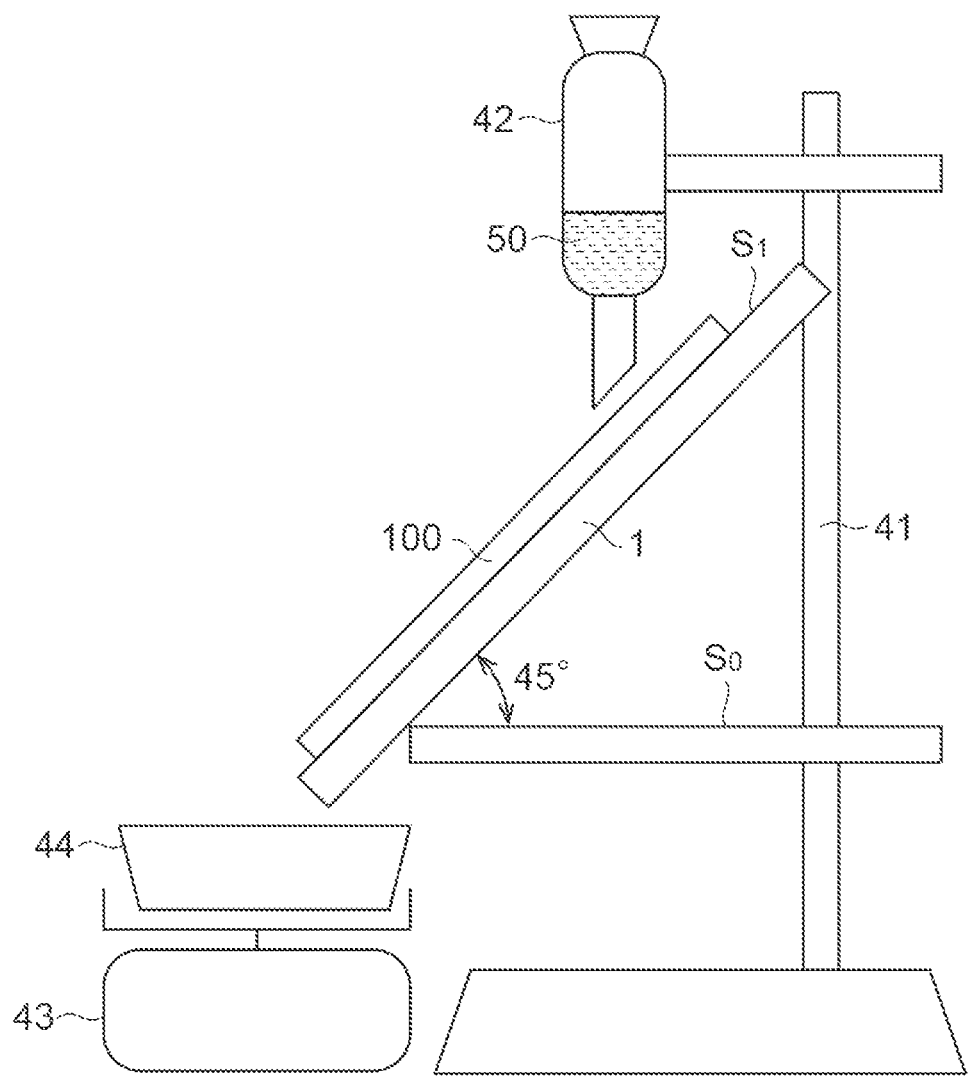
FIG. 2 is a schematic view showing a method for evaluating liquid leakage properties of an absorbent article.

FIG. 2 is a schematic view showing a method for evaluating leakage properties of an absorbent article. A support plate 1 (herein referred to as an acrylic resin plate, and hereinafter also referred to as an inclined plane $S_1$) with a length of 45 cm and having a flat main surface was fixed by a stand 41 in a state of being inclined at 45±2 degrees with respect to a horizontal plane $S_0$. An absorbent article 100 for testing was bonded onto the inclined plane $S_1$ of the fixed support plate 1 in a room at a temperature of 25±2° C. such that a longitudinal direction of the absorbent article 100 was along a longitudinal direction of the support plate 1, Next, a test solution 50 (artificial urine) adjusted to 25±1° C. was added dropwise from a dropping funnel 42 vertically disposed above the absorbent article toward a position 8 cm, in an upper direction, from the center of an absorbent in the absorbent article 100. 80 mL of the test solution was added dropwise at a time at a speed of 8 mL/sec. A distance between a tip end of the dropping funnel 42 and the absorbent article was 10±1 mm. The test solution was repeatedly added under the same conditions at intervals of 10 minutes from the start of the first addition of the test solution. The test solution was added until leakage was observed.

In a case where the test solution that was not absorbed by the absorbent article 100 leaked out from a lower part of the support plate 1, the leaked test solution was recovered in a metal tray 44 disposed below the support plate 1. A weight (g) of the recovered test solution was measured by a balance 43, and this value was recorded as an amount of leakage. The amount of leakage was subtracted from a total amount of the test solution added to calculate an amount of absorption until the leakage occurred. It is judged that as this numerical value becomes large, liquid leakage is unlikely to occur when the absorbent article is worn.

TABLE 3

| | Gradient absorption test | | | | | | | |
|---|---|---|---|---|---|---|---|---|
| | Amount of leakage [g] | | | | | | Number of addition until leakage occurs | Amount of absorption until leakage occurs [g] |
| Absorbent article | 1st | 2nd | 3rd | 4th | 5th | Total | | |
| Example 1 | 0 | 0 | 0 | 0 | 11 | 11 | 5 | 389 |
| Example 2 | 0 | 0 | 0 | 0 | 5 | 5 | 5 | 395 |
| Comparative Example 1 | 0 | 0 | 0 | 6 | 43 | 49 | 4 | 314 |
| Comparative Example 2 | 0 | 0 | 0 | 17 | 18 | 35 | 4 | 303 |

TABLE 3-continued

| | Gradient absorption test | | | | | | | |
|---|---|---|---|---|---|---|---|---|
| Absorbent article | Amount of leakage [g] | | | | | | Number of addition until leakage occurs | Amount of absorption until leakage occurs [g] |
| | 1st | 2nd | 3rd | 4th | 5th | Total | | |
| Comparative Example 3 | 0 | 0 | 0 | 8 | 35 | 43 | 4 | 312 |

Based on the results shown in Table 3, it can be said that the absorbent articles of Examples 1 and 2 are absorbent articles in which the occurrence of leakage is inhibited as compared with the absorbent articles of Comparative Examples 1 to 3.

REFERENCE SIGNS LIST

10: absorbent
10a: water-absorbing resin particle
10b: fiber layer
20a, 20b: core wrap
30: liquid-permeable sheet
40: liquid-impermeable sheet
50: test solution
100: absorbent article
$S_0$: horizontal plane
$S_1$: inclined plane

The invention claimed is:

1. Water-absorbing resin particles comprising:
a crosslinked polymer having a monomer unit derived from an ethylenically unsaturated monomer comprising at least one compound selected from the group consisting of (meth)acrylic acid and a salt thereof,
wherein a proportion of a (meth)acrylic acid and a salt thereof is 70 to 100 mol % with respect to a total amount of monomers in the crosslinked polymer,
a light transmittance at a wavelength of 425 nm when the water-absorbing resin particles are swollen 30 times with a physiological saline solution is 20% or more, and
a water retention capacity for the physiological saline solution is 30 to 55 g/g.

2. An absorbent article comprising:
a liquid-impermeable sheet;
an absorbent; and
a liquid-permeable sheet,
wherein the liquid-impermeable sheet, the absorbent, and the liquid-permeable sheet are disposed in this order, and
the absorbent comprises the water-absorbing resin particles according to claim 1.

3. The absorbent article according to claim 2, wherein the liquid-permeable sheet comprises thermal bonded non-woven fabrics, air through non-woven fabrics, resin bonded non-woven fabrics, spunbond non-woven fabrics, meltblown non-woven fabrics, airlaid non-woven fabrics, spunlace non-woven fabrics, point-bonded non-woven fabrics, or a laminate of two or more of non-woven fabrics selected from these non-woven fabrics.

4. The absorbent article according to claim 2, wherein the absorbent further comprises a fibrous material.

5. The absorbent article according to claim 2, further comprising a core wrap that covers at least a surface side of the absorbent in contact with the liquid-permeable sheet.

6. The absorbent article according to claim 5, wherein the core wrap is adhered to the liquid-permeable sheet.

7. The absorbent article according to claim 2,
wherein the absorbent is disposed to be in contact with the liquid-permeable sheet, and
the absorbent is adhered to the liquid-permeable sheet.

8. The absorbent article according to claim 2, wherein a water absorption speed of the water-absorbing resin particles for a physiological saline solution is 30 to 80 seconds.

9. The water-absorbing resin particles according to claim 1,
wherein the light transmittance at a wavelength of 425 nm when the water-absorbing resin particles are swollen 30 times with a physiological saline solution is 50% or more.

10. The water-absorbing resin particles according to claim 1,
wherein a median particle size of the water-absorbing resin particles is 250 to 850 μm.

\* \* \* \* \*